(12) United States Patent
Gono et al.

(10) Patent No.: US 8,162,828 B2
(45) Date of Patent: Apr. 24, 2012

(54) BLOOD CONTENT DETECTING CAPSULE

(75) Inventors: Kazuhiro Gono, Sagamihara (JP);
Takeshi Suga, Hino (JP)

(73) Assignee: Olympus Medical Systems Corp.,
Tokyo (JP)

( * ) Notice: Subject to any disclaimer, the term of this patent is extended or adjusted under 35 U.S.C. 154(b) by 1170 days.

(21) Appl. No.: 11/937,133

(22) Filed: Nov. 8, 2007

(65) Prior Publication Data

US 2009/0124874 A1    May 14, 2009

(51) Int. Cl.
*A61B 5/07* (2006.01)
*A61B 5/1459* (2006.01)

(52) U.S. Cl. .................. 600/302; 600/103; 600/476

(58) Field of Classification Search .................. 600/101, 600/103, 109, 112, 302, 341, 409, 424, 476
See application file for complete search history.

(56) References Cited

U.S. PATENT DOCUMENTS

| | | | |
|---|---|---|---|
| 5,604,531 A | 2/1997 | Iddan et al. | |
| 5,833,603 A * | 11/1998 | Kovacs et al. | 600/317 |
| 6,393,311 B1 * | 5/2002 | Edgar et al. | 600/323 |
| 6,639,674 B2 * | 10/2003 | Sokolov et al. | 356/369 |
| 6,640,117 B2 * | 10/2003 | Makarewicz et al. | 600/322 |
| 6,738,654 B2 * | 5/2004 | Sohrab | 600/345 |
| 7,118,529 B2 * | 10/2006 | Glukhovsky et al. | 600/160 |
| 7,468,044 B2 * | 12/2008 | Iddan | 600/584 |
| 7,492,935 B2 * | 2/2009 | Glukhovsky | 382/128 |
| 7,561,908 B2 * | 7/2009 | Glukhovsky et al. | 600/407 |
| 7,618,376 B2 * | 11/2009 | Kimball | 600/485 |
| 7,704,205 B2 * | 4/2010 | Mizuno | 600/118 |
| 7,724,928 B2 * | 5/2010 | Glukhovsky et al. | 382/128 |
| 7,792,344 B2 * | 9/2010 | Wang et al. | 382/128 |
| 7,914,442 B1 * | 3/2011 | Gazdzinski | 600/109 |
| 2004/0215068 A1 * | 10/2004 | Lykke et al. | 600/302 |
| 2004/0249245 A1 | 12/2004 | Irion | |
| 2006/0178557 A1 * | 8/2006 | Mintchev et al. | 600/104 |
| 2007/0088220 A1 * | 4/2007 | Stahmann | 600/485 |
| 2007/0106147 A1 | 5/2007 | Altmann et al. | |
| 2007/0129615 A1 | 6/2007 | Backman et al. | |
| 2007/0244402 A1 * | 10/2007 | Brockway et al. | 600/509 |
| 2008/0125623 A1 * | 5/2008 | Tamura et al. | 600/101 |

FOREIGN PATENT DOCUMENTS

| | | |
|---|---|---|
| CN | 1678239 | 10/2005 |
| KR | 10-2003-0071820 | 9/2003 |
| KR | 10-2007-0047221 | 5/2007 |
| WO | 02/055984 | 7/2002 |
| WO | 2004322621 | 4/2004 |
| WO | WO 2004/032621 | 4/2004 |
| WO | WO 2005/039402 | 5/2005 |
| WO | WO 2005/113021 | 12/2005 |

* cited by examiner

*Primary Examiner* — Francis Jaworski (57) ABSTRACT

A capsule employing components for detecting blood content or hemoglobin concentration within tissue forming a lumen in vivo advantageously permits screening or diagnosis of certain diseases. In one embodiment, the capsule includes a light source for intermittently illuminating a region of tissue and a light detector for receiving interacted light from the tissue and hemoglobin therein. Methods of validating data of interacted light signal are also disclosed. A power conservation method of detecting the blood content values at different rates is further disclosed.

7 Claims, 10 Drawing Sheets

BLOOD CONTENT DETECTING CAPSULE

CROSS REFERENCE TO RELATED APPLICATIONS

This application is related to U.S. patent application Ser. No. 11/937,185, filed Nov. 8, 2007, entitled "Capsule Blood Detection System and Method" and U.S. patent application Ser. No. 11/937,153, filed Nov. 8, 2007, entitled "Method and System for Correlating Image and Tissue Characteristic Data," both of which are incorporated by reference herein.

FIELD OF THE INVENTION

This invention relates to a capsule having functionality for detecting the blood content in tissue within the digestive tract of an organism.

BACKGROUND OF THE INVENTION

Scientists have discovered that a detectible increase in the blood content of superficial mucous membrane occurs proximate cancerous and precancerous lesions in the colon relative to the blood content of healthy tissue as described in, for example, R. K. Wali, H. K. Roy, Y. L. Kim, Y. Liu, J. L. Koetsier, D. P. Kunte, M. J. Goldberg, V. Turzhitsky, and V. Backman, *Increased Microvascular Blood Content is an Early Event in Colon Carcinogenesis,* Gut Vol. 54, 654-660 (2005), which is incorporated by reference herein. This phenomenon is referred to as early increase in blood supply (EIBS).

Currently, there are no known capsule devices for detecting blood content in the colon or other lumens of an organism. There are capsule endoscopes that provide images of the inside of a gastrointestinal tract or other regions along the digestive tract. These capsule endoscopes are small enough to be swallowed by a person or animal. They generally includes an image capture device such as a CCD device. Capsule endoscopes enable alternative diagnostic and screening procedures relative to conventional endoscopes for detecting diseases in the digestive tract such as gastroesophagus reflux and gastric ulcers. Such procedures are less invasive than conventional endoscopes which use a long, thin tube inserted through the esophagus, small intestine, colon, and rectum. Known capsule endoscopes capture images but do not provide blood content information of tissue along the digestive tract.

It is desirable to have a non-invasive device or method for detecting the blood content of the tissue along the digestive tract for screening or diagnosis of particular diseases and for other purposes.

SUMMARY OF THE INVENTION

According to the invention, the sensing of blood content or hemoglobin (Hb) concentration in living tissue that form a lumen of an organism is performed by a capsule-type sensing device depositable within the lumen and a receiver/processing unit for receiving a signal from the capsule indicative of detected blood content. A technique for detecting the hemoglobin Hb concentration using polarized light has been disclosed in Y. L. Kim, Y. Liu, R. K. Wall, H. K. Roy, M. J. Goldberg, A. K. Kromin, K. Chen, and V. Backman, *Simultaneous measurement of angular and spectral properties of light scattering for characterization of tissue microarchitecture and its alteration in early precancer,* IEEE J. Sel. Top. Quant. Elec., Vol. 9, 243-256 (2003) and M. P. Siegel, Y. L. Kim, H. K. Roy, R. K. Wali, and V. Backman, *Assessment of blood supply in superficial tissue by polarization-gated elastic light-scattering spectroscopy,* Applied Optics, Vol. 45, 335-342 (2006) and the entirety of those articles are incorporated herein by reference. In one exemplary embodiment of the present invention, a capsule includes a light source for illuminating a region of tissue, a light detector for receiving interacted light from the tissue and blood therein, and a controller for controlling the intervals at which the sensing device detecting the blood content. In another aspect of the invention, the controller is responsive to the output of an evaluation unit which determines when the detected blood content signal satisfies a condition, such as, for example, when the sensed blood content is greater than a predetermined threshold value. The capsule may also include an image capture device for capturing corresponding images of the living tissue that form a lumen.

According to another aspect of the invention, the capsule includes a data validator for validating signals from the light detector that are generated by the detected interacted light from an illuminated region of tissue. For example, the capsule may generate unsound or illogical data, i.e., invalid data, when its sensor is not located within advantageous position in the digestive tract. The capsule may further advantageously include a location indicator, e.g. organ sensor, for indicating which organ of the digestive tract from which the capsule is obtaining blood content information. The location indicator can be a variety of different types, such as a pH level sensor, color sensor, temperature sensor, time sensor, pressure sensor, or magnetic sensor.

According to yet another aspect of the invention, a method for validating the detected blood content characteristic is disclosed. A blood content characteristic is detected and measured at a first predetermined intermittent manner. When the detected blood content satisfies a certain condition, e.g., greater than a predetermined threshold, a plurality of blood content measurements are performed in a more rapid succession. These measurements are then statistically evaluated relative to a condition to determine if the detected characteristics represent a valid Hb concentration and not illogical data.

DETAILED DESCRIPTION OF THE INVENTION

Figure 1:
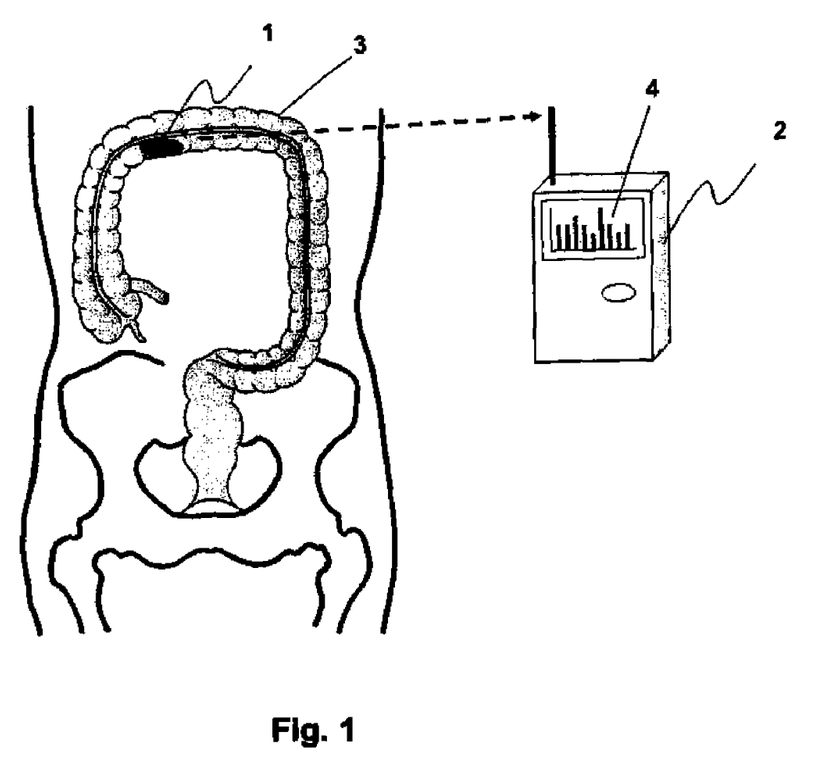
FIG. 1 is a schematic view of an exemplary system in accordance with the invention.

FIG. 1 shows a schematic view of an exemplary blood content sensing system in accordance to the present invention. As seen in FIG. 1, the system includes a capsule-type sensing device 1 (hereinafter "capsule") and a receiver/processing unit 2. In FIG. 1, the capsule 1 is shown disposed in an example region of a colon 3 of a patient. It should be understood that the capsule 1 may be swallowed or disposed in the digestive tract by other means. The capsule 1 may further be moved along the digestive tract by peristolysis. The capsule 1 detects a characteristic indicative of blood content, i.e., the hemoglobin (Hb) concentration, at one or more tissue regions along the digestive tract, such as the colon, and transmits the data to the processing unit 2. As is also shown in FIG. 1, the processing unit 2 may be located external to the patient. The processing unit 2 analyzes data received from the capsule 1 and displays the results on a display 4.

The capsule 1 is shown having an elliptical shape in cross-section, but other shapes may be employed. However, shapes that facilitate swallowing by a patient or depositing of the capsule 1 inside a lumen of a living organ are preferable. FIG. 1 also shows the capsule 1 being located in the colon of a human-being. However, it should be understood that the capsule 1 is useable in animals. Also, the present invention is described with regard to the detection of blood content in the superficial mucosa of the colon for illustration purposes only. However, it should be understood that the capsule 1 can also be used to detect the blood content of superficial or deeper tissue portions in other areas of the digestive tract or other lumens of a living body Furthermore, the data transmission between the capsule 1 and processing unit 2 occurs when the capsule 1 is positioned within a patient is also only for illustration purposes. It is also possible according to the invention to employ means for storing blood content data in the capsule 1 and extracting the data at a subsequent time, rather than sending the data to the processing unit 2.

Figure 2:
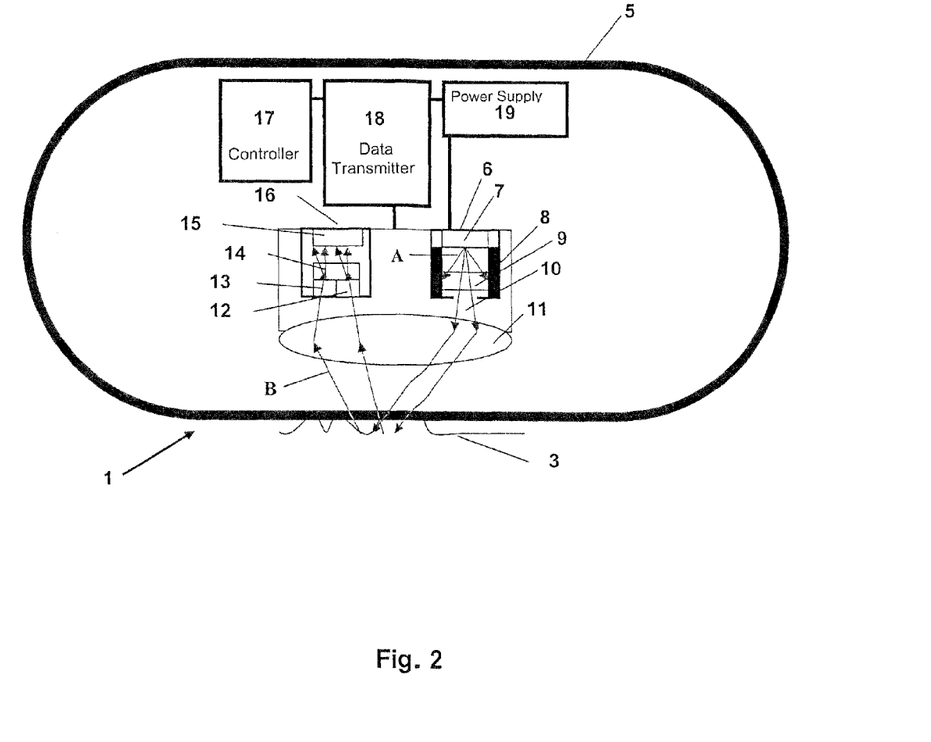
FIG. 2 is an exemplary structure of a capsule-type sensing device according to a first embodiment of the invention.

FIG. 2 shows an exemplary structure of a capsule in accordance with the invention. As seen in FIG. 2, the capsule 1 comprises a capsule enclosure 5 in contact with the surface of a portion of the tissue 3. The components encased within the enclosure 5 include a light source 6, a lens 11, a light detector 16, a controller 17, a data transmitter 18, and a power supply 19. The light source 6 produces polarized light to illuminate a small region of tissue 3. As stated, a technique for using polarized light for determining hemoglobin content has been disclosed in U.S. Published Patent Application 2007/0129615 of Blackman et al, published Jun. 7, 2007 and U.S. Published Patent Application 2007/0179368 of Blackman et al, published Aug. 2, 2007 and the entirety of those published patent applications are hereby incorporated herein by reference. An exemplary configuration for such a light source 6 is depicted in FIG. 2 In FIG. 2, polarized light is produced using, for example, a white LED, linear polarizer 9 and opening 10. Light absorbing surfaces 8 are disposed between the LED 7 and opening 10 and surround the light polarizer 9.

The light detector 16, for example, comprises a first linear polarizer 12, a second linear polarizer 13, a transmissive grating 14 and a light sensor 15, wherein the polarization angles for the first and second polarizers are orthogonal to each other and pass respective beams of polarized light perpendicular to each other. The polarization direction of the first linear polarizer 12 is the same as that of the linear polarizer 9 in the light source 6, and the polarization direction of the second linear polarizer 13 passes through the polarization spectrum orthogonal thereto.

In operation, the light generated from the LED 7 travels in the direction of arrows A. Light generated by LED 7 that does not pass through polarizer 9 is absorbed by light absorbing surfaces 8. The opening 10 of the light source 6 is positioned along the focal length of the lens 11 such that the light produced by the light source 6 is a narrow-angle, substantially polarized, light impinging on a small region of the tissue 3. Furthermore, by employing different shape or oriented lens for the lens 11, it is possible to alter the direction in which the light emitted from the light source 6 travels.

A portion of light that interacts with the tissue 3 and the Hb concentration contained therein returns along the direction of the arrows B to the light detector 16. The interacted light returned to the detector 16 includes polarized light at particular angles of orientation. The interacted light received from the tissue 3 travels through the first and second polarizers 13, 14 and transmissive grating 14. The polarizers 13, 14 have orthogonal orientations relative to one another. As a consequence, light emitting from the polarizers 13, 14 represent substantially polarized light in the respective orthogonal angles based on the polarized angle of orientation of the received interacted light B. The grating 14 diverts the respective polarized light components to different regions of the light sensor 15. The light sensor 15 performs spectroscopy in two kinds of polarization states, i.e., the first or horizontal polarization spectrum and the perpendicular polarization spectrum. Signals indicative of the measured spectrum data from the light sensor 15 are then transmitted by the data transmitter 18 to the processing unit 2 of FIG. 1.

It is suitable for the data transmitter 18, for example, to calculate a difference between the first or horizontal polarization spectrum and the perpendicular polarization spectrum and transmits the result to the processing unit 2. It is alternatively suitable in accordance with the invention for the difference operation to be carried out in the processing unit 2 or other external device whereby data indicative of the horizontal polarization spectrum and the perpendicular spectrum are sent to the processing unit 2 by the capsule 1.

The capsule 1 also includes a controller 17 for controlling the activation timing of the light source 14, light detector 16 and/or the data transmitter 18 to acquire blood content information and transmit corresponding data to the processing unit 2. The power supply 19 powers the components of the capsule 1.

Figure 3:
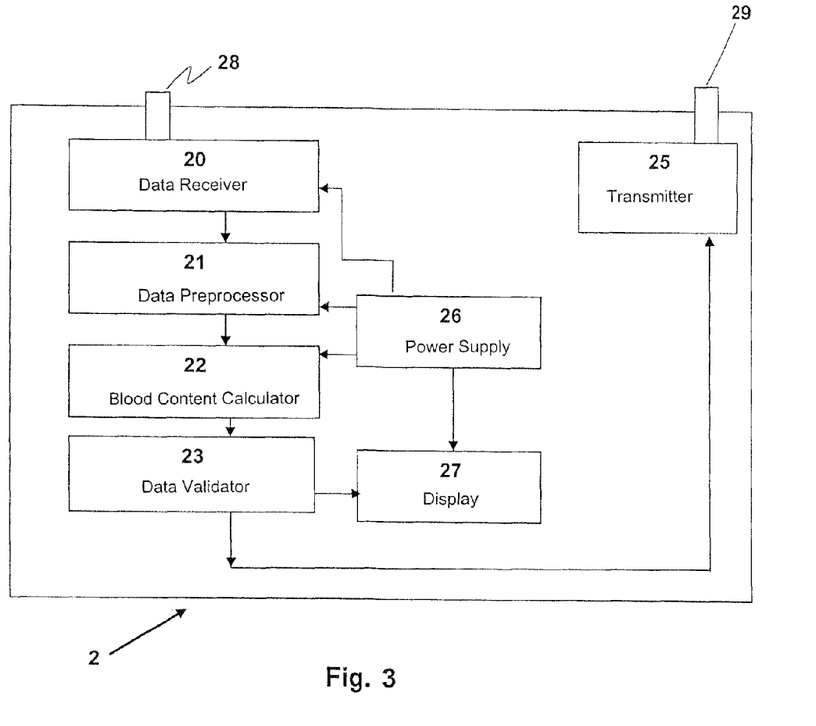
FIG. 3 is a block diagram of an exemplary processing unit for use with the sensing device of FIG. 2.

FIG. 3 shows an exemplary block diagram of the processing unit 2 in FIG. 1. In the embodiment depicted in FIG. 3, the processing unit 2 includes a data receiver 20, a data preprocessor 21, a blood content estimator 22 (or blood content calculator), a data validator 23, a transmitter 25, a power supply 26, and a display 27. The data receiver 20 comprises a wireless reception component 28, such as a conventional RF receiver, for receiving the data signal from the capsule 1 of FIG. 2. In the alternative, data transmission and reception using alternative techniques such as acoustic or infrared schemes are likewise useable in accordance with the invention. In such case, a data transmitter 18 in the capsule 1 and a data receiver 20 in the processing unit 2 would be provided with components that conform to the acoustic or infrared technology, accordingly.

In operation, the data received by the data receiver 20 is provided to a data preprocessor 21. The data preprocessor 21 executes, for example, a data correction algorithm, such as white correction represented in the following equation (1).

$$\Delta lc(\lambda) = \Delta l(\lambda)/\Delta lw(\lambda) = (l_\|(\lambda) - l\perp(\lambda))/(lw_\|(\lambda) + lw\perp(\lambda)) \quad (1)$$

In equation (1), $\lambda$ represents wavelength. $\Delta l(\lambda)$ indicates the measured difference polarization spectrum. $\Delta lw(\lambda)$ is a spectrum measured by using what is known as a standard white plate and is calculated by summing the white horizontal polarization spectrum $lw_\|(\lambda)$ and the white perpendicular polarization spectrum $lw_\perp(\lambda)$, as shown in the denominator of equation (1). In the numerator of equation (1), the difference between the horizontal polarization spectrum $l_\parallel(\lambda)$ and the perpendicular polarization spectrum $l_\perp(\lambda)$ is calculated in data transmitter 18 and a signal indicative of $\Delta l(\lambda)$ is transmitted by data transmitter 18 to the processing unit 2.

The blood content estimator 22 calculates the blood content by using equation (2) below, which is shown in, for example, M. P. Siegel, Y. L. Kim, H. K. Roy, R. K. Wali, and V. Backman, *Assessment of blood supply in superficial tissue by polarization-gated elastic light-scattering spectroscopy*, Applied Optics, Vol. 45, 335-342 (2006).

$$\Delta l(\lambda) = \Delta l_{scattering}(\lambda)\exp[-\alpha A_{PG}(\lambda)] \qquad (2)$$

As stated, the blood content estimator 22 calculates the blood quantity by using a model equation, such as equation (2), and provides a corresponding blood content value to an indicator such as display 27. The corresponding blood characteristic information can then be displayed to the user by display 27. In addition there is a power supply 26 to power the components in the processing unit 2.

The data validator 23 compares the estimated blood content against, for example, a threshold value. When the estimated blood content is greater than the threshold value, the region of the tissue where the blood content is detected may have an EIBS condition. Conversely, when the estimated blood content is lower than the threshold, the region is believed not to have an EIBS condition. In this exemplary embodiment, when the estimated blood content is greater than the threshold, i.e., believed to have an EIBS condition, the transmitter 25 of the processing unit 2 transmits a signal to the controller 17 of the capsule 1 of FIG. 2 via antenna 29. In response, the controller 17 controls the data transmitter 18 in the capsule 1 such that the time interval for acquiring blood content data increases.

Figure 4:
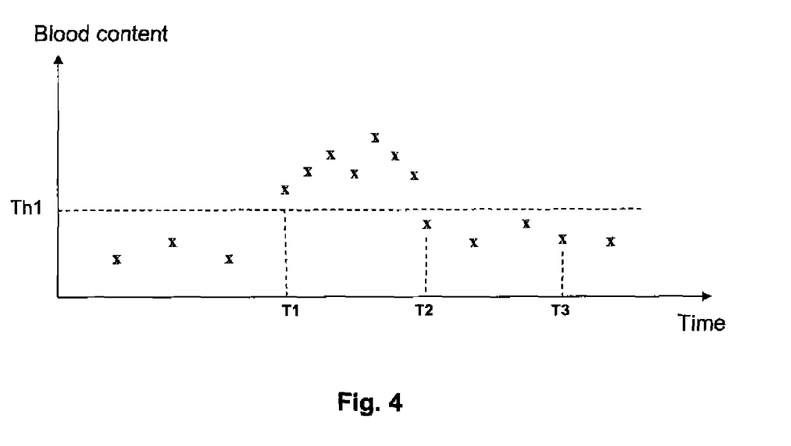
FIG. 4 is a graph of representative blood content data relative to data acquisition time taken by the capsule of FIG. 2.

FIG. 4 shows an exemplary graph of the blood content data relative to blood content detection or data acquisition time performed by the capsule 1. As seen in FIG. 4, each data measurement at a respective time is indicated by an "X". When the blood content data is greater than a threshold Th1, the time interval for detecting the blood content is shortened relative to when the detected blood content is lower than the threshold Th1 as represented as a comparison between time intervals T1-T2 having blood content data greater than the threshold Th1 and time interval T2-T3 with blood content data less than the threshold Th1. In accordance with this variable measurement technique, the life of the battery of power supply 19 is advantageously prolonged.

Figure 5:
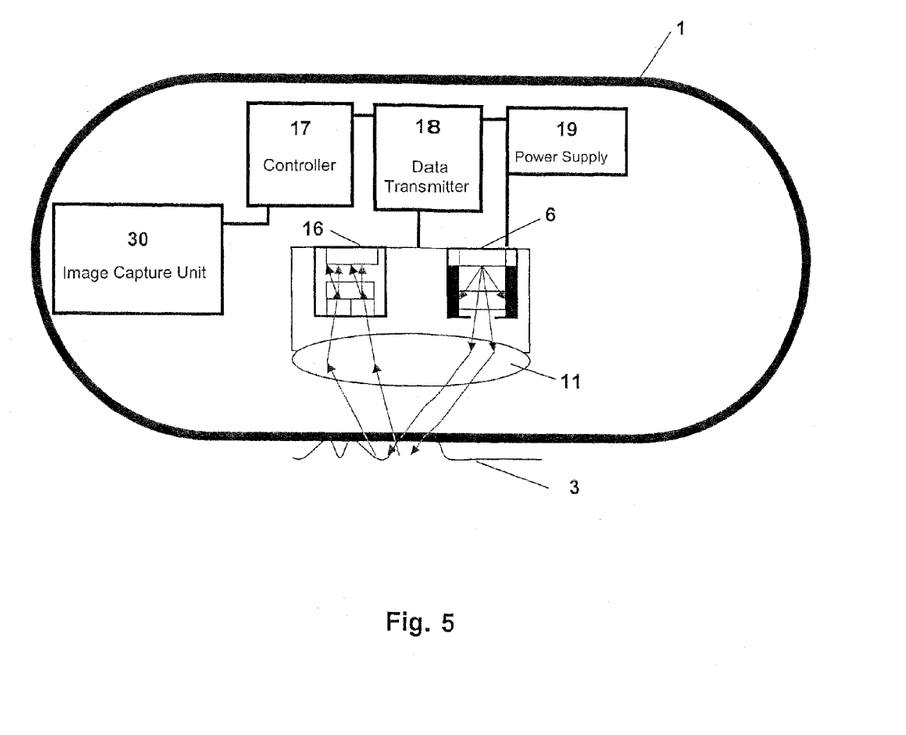
FIG. 5 is a block diagram of an alternative embodiment of a capsule according to the invention.

FIG. 5 shows a block diagram of an alternative embodiment of the capsule 1 according to the present invention. The difference between the capsule 1 in FIG. 2 and that in FIG. 5 is that in FIG. 5 the capsule further comprises an image capture unit 30 for capturing images of the tissue 3. The imaging unit 30 is preferably structured such that the in vivo images are acquired in synchronization with the acquisition of spectrum information data. The particular components chosen for the image capture unit 30 is not critical to practicing the present invention and any image capture devices that may fit into and operate within a capsule may be employed. Suitable components for the image capture unit 30 are those found in other capsule endoscopes including, for example, the endoscope disclosed in U.S. Pat. No. 7,229,407 assigned to Olympus Corp., which is incorporated herein by reference. As can be readily understood, the combination of blood content detection and corresponding image capture functionality is an advantageous diagnostic tool that facilitates the detection of certain diseases, such as tumors within the digestive tract with corresponding EIBS exhibited in surrounding tissue.

Figure 6:
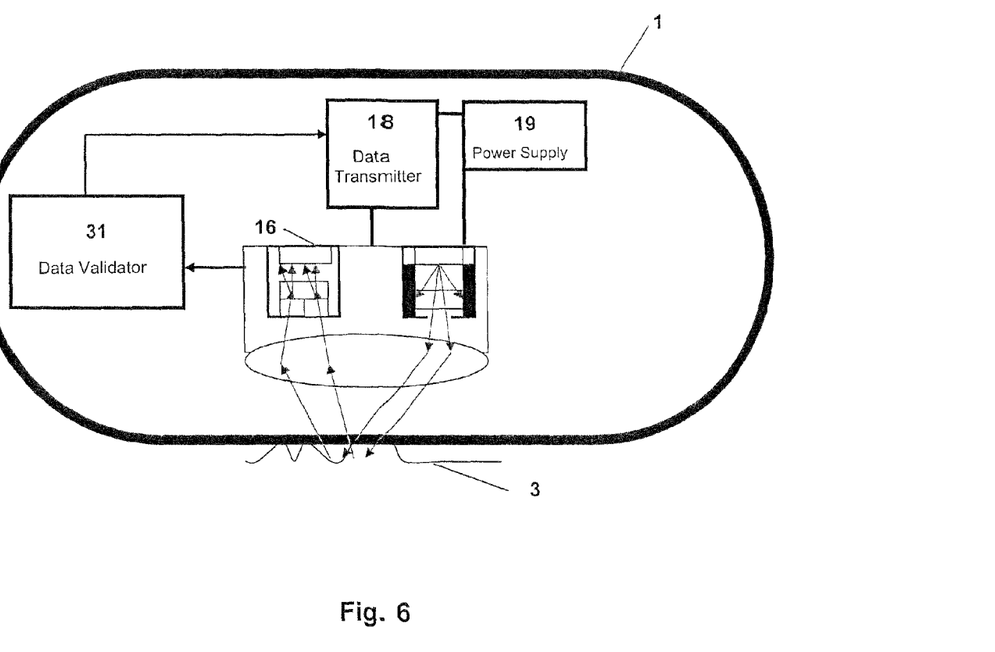
FIG. 6 is a block diagram of another embodiment of a capsule according to the invention.

Turning now to FIG. 6, FIG. 6 is a block diagram showing another exemplary embodiment of the capsule 1 according to the present invention. The difference of the capsule in FIG. 6 relative to those of FIGS. 2 and 5 is that FIG. 6 further comprises a data validator 31 coupled to the light detector 16. The light detector 16 of FIG. 2 detects blood content accurately when the capsule 1 is in contact with or close proximity to the tissue surface. Thus, in this embodiment, blood content data values produced when the capsule 1 is in contact with or close proximity to tissue is considered valid. Suitable distances for measurement include, for example, 0 to 1 mm. When the capsule 1 is located at a disadvantageous distance from the tissue surface, the measured data would represent illogically low blood content and would be invalid. The validity of the data is determined by following equation (3):

$$l_\parallel(\lambda) + l_\perp(\lambda) < Th2 \qquad (3)$$

If the sum of the perpendicular polarization spectrum $l_\perp(\lambda)$ and the horizontal polarization spectrum $l_\parallel(\lambda)$ of a specific wavelength is less than a predetermined threshold Th2, the measured data is considered to be invalid. Consequently, the data validator 31 sends a signal to the data transmitter 18 indicating that the data is invalid. Conversely, when the sum is greater than the threshold Th2, the data is considered valid. When the data is valid, the valid data is sent from the light receiver 16 to the data transmitter 18.

Figure 7:
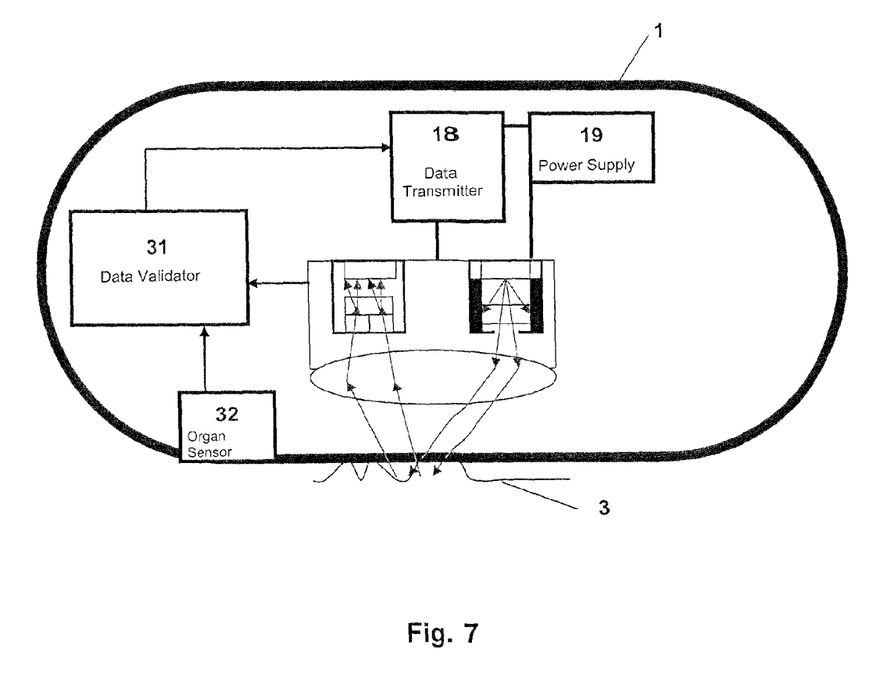
FIG. 7 is a diagram of a further embodiment of a capsule according to the invention.

FIG. 7 shows a block diagram of yet another exemplary capsule in accordance to the present invention. Relative to the capsule 1 of FIG. 6, the capsule 1 of FIG. 7 further comprises an organ sensor 32 for the location of the capsule 1 in the digestive tract. As an example, the organ sensor in FIG. 7 is a pH sensor 32. The pH sensor 32 is used because the pH level is different among the esophagus, stomach, duodenum, small intestine, and colon. The pH sensor 32 intermittently measures the pH level of the living body and provides the results, for example, to the data validator 31. In response to the detected pH level, the data validator 31 may determine whether or not the capsule 1 has entered, for example, the colon. If the data validator 31 determines that the capsule 1 has entered the colon, then a signal is sent to the data transmitter 18 to the processing unit 2 of FIG. 1.

Although the embodiment of FIG. 7 includes a pH sensor 32, other types of sensors, such as a color sensor, temperature sensor, time sensor, pressure sensor, or magnetic sensor, can be used themselves or in addition to the pH sensor.

Figure 8:
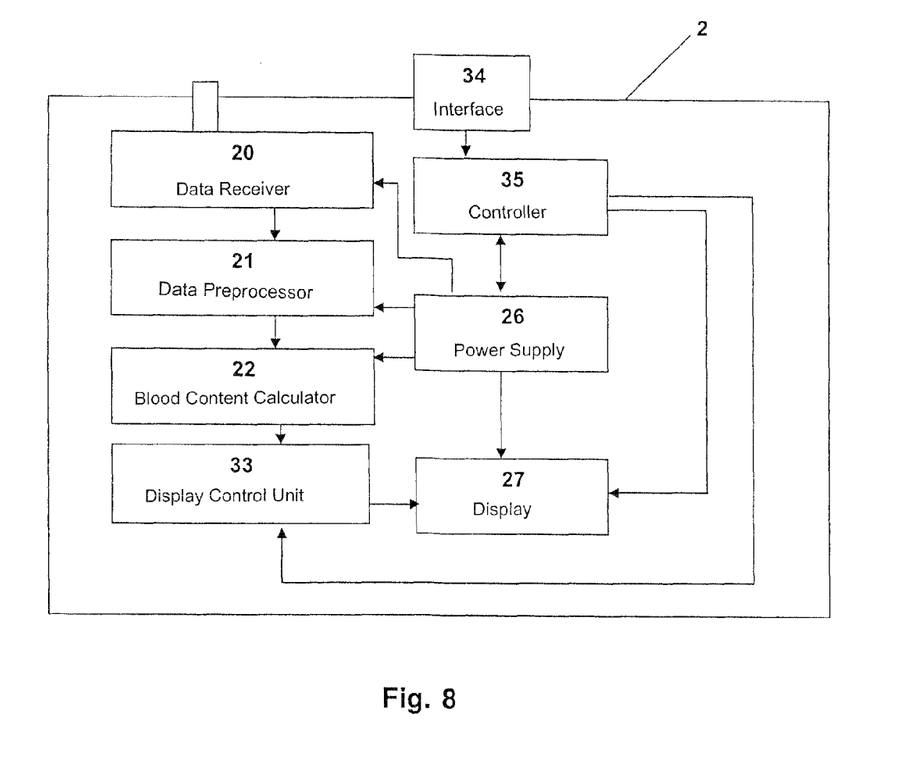
FIG. 8 is a block diagram of an exemplary processing unit according to the invention for the sensing device of FIG. 6.

FIG. 8 shows an exemplary circuit diagram useable for the processing unit 2. The processing unit 2 in FIG. 8 is similar to that in FIG. 3, except the unit in FIG. 8 does not include a data validator. As such, all data is sent to the display without being compared with a threshold. Furthermore, the processing unit 2 in FIG. 8 includes display control unit 33. The display control unit 33 allows an operator, such as a clinician, doctor or nurse, to create specific types of information and data to be shown on the display 27. The processing unit 2 in FIG. 8 also includes an interface 34 for the operator to control the controller 35 which controls the display 27 and the display control unit 33.

Figure 9:
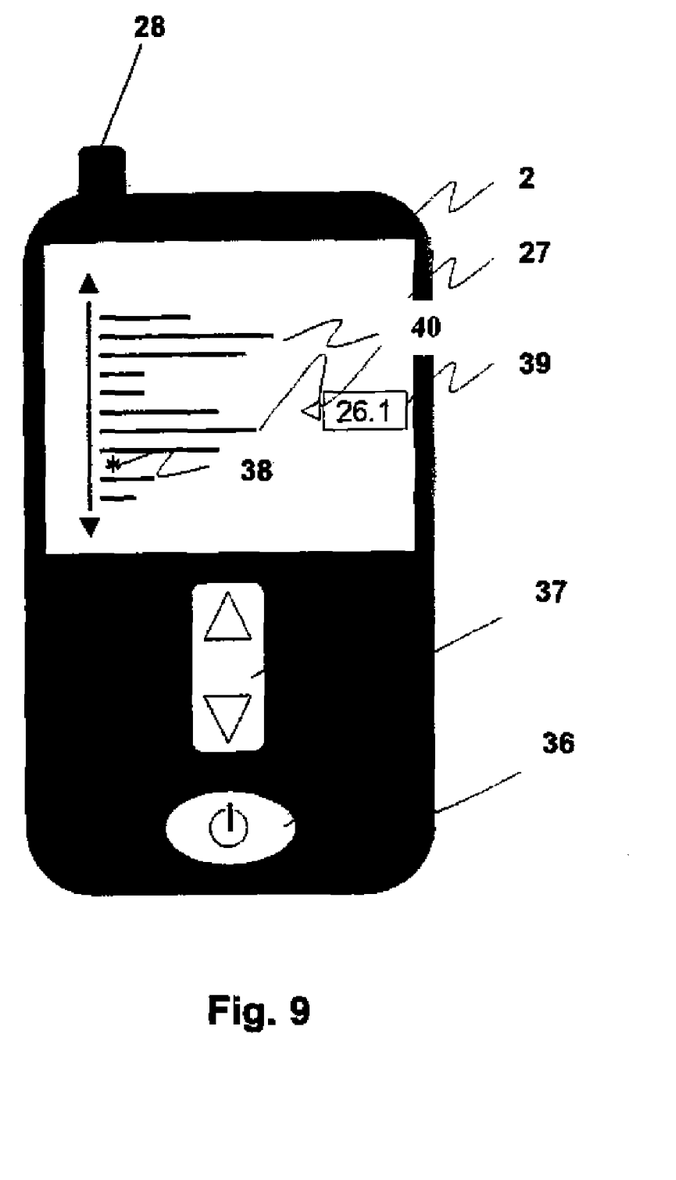
FIG. 9 is a diagram of an exemplary hand-held processing unit according to the invention.

FIG. 9 shows a diagram of an exemplary hand-held version of processing unit 2. In this embodiment, a power supply button 36 and a scroll button 37 are provided as the interface 34 of FIG. 8. Furthermore, an LCD monitor is provided as display 27. The display 27 shows the Hb concentration, or blood content, by a bar graph 40. In an exemplary operation, when a calculated Hb concentration is above a threshold value, a bar having a length indicative of HB concentration is displayed. If the calculated Hb concentration is below the threshold value, a corresponding symbol, such as an "*" 38, is displayed. In this embodiment, data is sequentially displayed from top down and old data disappears from the top. The relationship between the data update and data arrangement in the display can alternatively be reversed. It is additionally possible to show old data that has disappeared from the screen by using the scroll button. An actual number 39 representing a bar may also be shown.

During or after the capsule 1 has passed through a patient's digestive tract, a clinician views the bar graph of the Hb concentration recorded and displayed on the processing unit 2 and judges the possible existence of certain corresponding diseases, such as lesions or tumors, in the digestive tract. For example, if the Hb concentration shows the trend similar to the two maximum values of the Hb concentration 40 in FIG. 9, at least two tumors may exist. Accordingly, the operator can recommend to the patient to have a colon endoscopy and other subsequent measures. Note that even though the processing unit is shown in FIG. 8 as a hand held device, it can be any kind of display, portable, fixed, or otherwise. In this manner, the blood content detection capsule in accordance with the invention operates as an advantageous screening tool.

Figure 10:
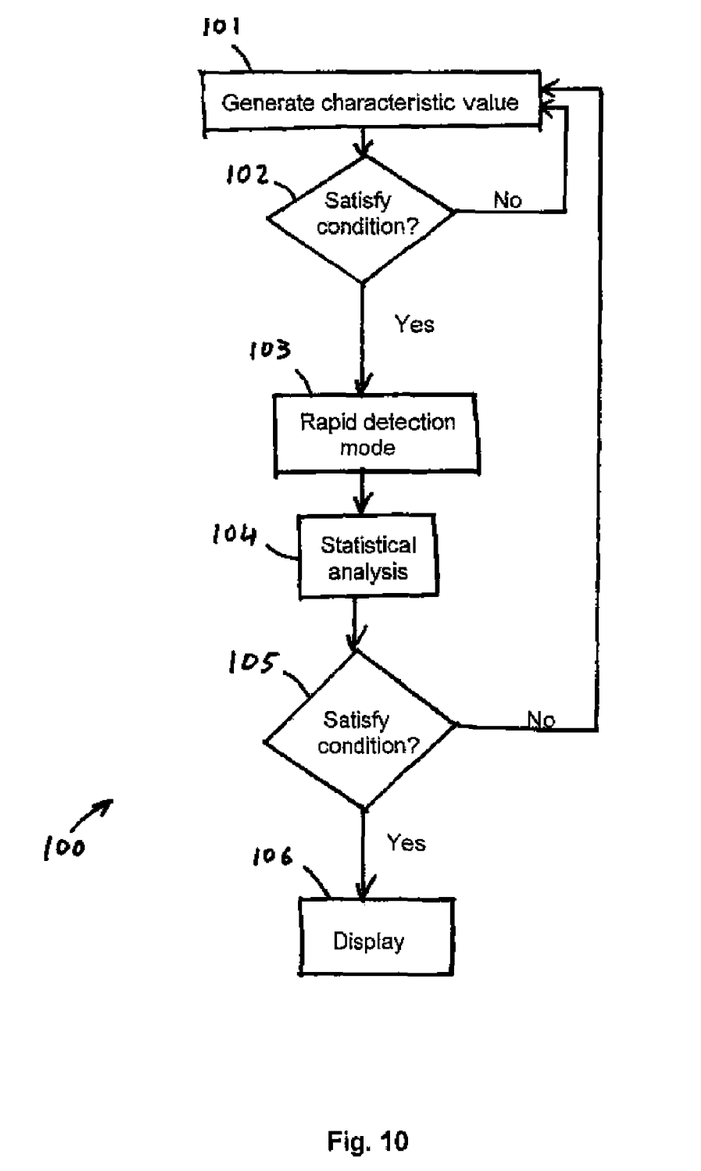
FIG. 10 is a flow diagram of a method for validating measured data according to one embodiment of the invention.

FIG. 10 shows a flow diagram 100 of an exemplary method for validating detected Hb concentration data according to another embodiment of the invention. The flow diagram 100 of FIG. 10 is described with regard to the capsule 1 in any of FIGS. 2, 5, 6, or 7. In step 101, the capsule 1 detects a characteristic value based on a signal generated from light detector 16 of Hb concentration in a region of tissue 3. Steps 102 to 105 then determines if that generated characteristic represents a valid Hb concentration. In step 102, a determination is made whether the generated characteristic value satisfies a certain condition, such as a predetermined threshold. If the condition is not met, e.g., the generated characteristic value is below the predetermined threshold, then the value is considered not to represent Hb concentration and the capsule 1 performs step 101 to detect the characteristic value generated by the light detector 16 at another region of tissue. Conversely, in step 102, if the condition is satisfied, e.g., the generated characteristic value by the light detector 16 is greater than the predetermined threshold, then the capsule 1 will enter a more rapid detection mode in step 103, wherein the capsule 1 collects a plurality of characteristic values based on substantially the same illuminated tissue region within a shortened time period.

In step 104, the values generated during the more rapid detection mode are then statistically analyzed, e.g., determination of a corresponding mean value. Then, in step 105, the result of the statistical analysis of step 104 is evaluated relative to satisfying a condition, e.g., the threshold determination employed in step 102. In step 105, if the condition is not satisfied, then it is determined that the generated characteristic values during the more rapid detection mode do not represent valid Hb concentration and the process again returns to step 101 to detect the characteristic value generated by the light detector 16 at another region of tissue. Conversely, in step 105, if the condition is satisfied, then it has been determined that one or more generated characteristic values are valid in representing Hb concentration. In step 106, a corresponding indication is provided for the Hb concentration, e.g., displayed, for the clinician. After step 106 is performed, the method 100 again returns to step 101 to detect the characteristic value generated by the light detector 16 at another region of tissue.

In the process of FIG. 10, the predetermined threshold in box 104 is, for example, a value of a predetermined blood content average based on healthy tissue of a population of subjects with no tumors or EIBS. It should be understood that other threshold values or statistical determinations are alternatively useable in accordance with the invention. For instance, a suitable alternative statistical evaluation includes the predetermining threshold determining by subtracting the standard deviation from the predetermined blood content average. The standard deviation is calculated from data resulted from the more rapid detections described with respect to FIG. 10.

According to another exemplary embodiment of the present invention, the method of validating measured blood content as shown in FIG. 10 also includes the step of comparing the standard deviation with a predetermined threshold. If the standard deviation is excessive compared to the threshold, then it can be judged that the capsule is not in contact with the tissue or is in some other situations unstable for detecting the blood content. In such a case, the detected data may be concluded as invalid. Furthermore, it should be understood that in addition to standard deviation, other types of statistical calculation of data, such as a root mean square determination or a predetermined range of data values, may be used as alternatives to step 107 in the validation method of FIG. 10.

With the exemplary capsule 1 disclosed in FIGS. 2, 5, 6, and 7 and the exemplary processing unit 2 in FIGS. 3, 8, and 9, either alone or in combination, EIBS conditions in the digestive tract and other lumens in patients can be detected. The information related to the EIBS conditions is a useful tool for screening of cancerous or precancerous conditions of lesions, tumors, or other diseases. Doctors or clinicians may use such information to determine further diagnosis or treatments.

From the embodiments of the invention described above, it should be understood that the present invention is not limited to those disclosed embodiments. Various changes and modifications thereof could be made by one of ordinary skill in the art without departing from the spirit or scope of the invention.

What is claimed is:

1. A system for detecting blood content in living tissue comprising:
   a capsule disposable in a lumen of a living organism, said capsule comprising a detector for detecting a characteristic indicative of blood content of tissue forming the lumen, a transmitter, and a controller for controlling time intervals at which the detector generates a signal indicative of the characteristic, the controller being coupled to the detector;
   a processing unit comprising a receiver for receiving a signal transmitted by the transmitter; and
   a data validator for generating a control signal based on whether the signal indicative of the characteristic satisfies a predetermined condition, wherein the controller is capable of adjusting intermittent time intervals at which the detector detects the characteristic based on the control signal output from the data validator such that when the detected characteristic indicative of the blood content is greater than the predetermined condition of a threshold value, the controller shortens the time intervals for detecting the blood content relative to when the detected characteristic indicative of the blood content is lower than the threshold value.

2. The system as claimed in claim 1, wherein the capsule further comprises:
   a light source for illuminating a tissue location; and a sensor provided in the detector so that the detector detects interacted light from the tissue location and generates a signal indicative of said characteristic.

3. The system as claimed in claim 1, wherein the data validator is disposed in said capsule.

4. The system as claimed in claim 1, wherein the data validator is disposed in said processing unit.

5. The system of claim 1, wherein the controller controls an activation timing of the transmitter to transmit information related to a characteristic indicative of blood content to the processing unit.

6. The system of claim 1, wherein the data validator determines based on a predetermined threshold value whether a characteristic value related to the characteristic detected by the detector is valid.

7. The system of claim 1, further comprising:
a blood content estimator for calculating a blood content based on the characteristic detected by the detector, wherein the data validator determines based on a predetermined threshold value whether data of the blood content calculated by the blood content estimator is valid.

\* \* \* \* \*